United States Patent [19]
Koopmann

[11] Patent Number: 5,133,340
[45] Date of Patent: Jul. 28, 1992

[54] CLAVICLE BANDAGE

[75] Inventor: Jens-Wolfgang Koopmann, Reppenstedt, Fed. Rep. of Germany

[73] Assignee: Beiersdorf Aktiengesellschaft, Hamburg, Fed. Rep. of Germany

[21] Appl. No.: 641,191

[22] Filed: Jan. 15, 1991

Related U.S. Application Data

[63] Continuation of Ser. No. 461,722, Jan. 8, 1990, abandoned.

[30] Foreign Application Priority Data

Jan. 24, 1989 [DE] Fed. Rep. of Germany ....... 3901918

[51] Int. Cl.⁵ ............................................. A61F 5/04
[52] U.S. Cl. .......................................... 602/19; 2/44; 2/45
[58] Field of Search ................ 128/87 R, 78; 2/45, 2/44

[56] References Cited

U.S. PATENT DOCUMENTS

| | | | |
|---|---|---|---|
| 370,055 | 9/1887 | Haley | 2/45 |
| 698,085 | 4/1904 | Wander et al. | 2/45 |
| 1,050,257 | 1/1913 | Trigg | 2/45 |
| 2,233,397 | 3/1941 | Bloom | 119/96 |
| 2,450,298 | 9/1948 | Peterson et al. | 128/87 R |
| 3,141,456 | 7/1964 | Meek | 128/87 R |
| 3,382,868 | 5/1968 | Stiefel | 128/87 R |
| 3,467,085 | 9/1969 | Cormier | 128/876 |
| 3,499,441 | 3/1970 | Hall | 128/87 R |
| 3,548,818 | 12/1970 | Kaplan | 128/87 R |
| 3,718,137 | 2/1973 | Gaylord, Jr. | 128/87 R |
| 3,856,004 | 12/1974 | Cox | 128/87 R |
| 3,857,388 | 12/1974 | Frankel | 128/87 R |
| 3,897,776 | 8/1975 | Gaylord, Jr. | 128/87 R |
| 4,589,406 | 5/1986 | Florek | 128/87 R |

FOREIGN PATENT DOCUMENTS

| | | |
|---|---|---|
| 746928 | 8/1970 | Belgium . |
| 149465 | 7/1981 | Fed. Rep. of Germany . |
| 259349 | 3/1982 | Fed. Rep. of Germany . |
| 8900721 | 3/1989 | Fed. Rep. of Germany . |
| 840015 | 4/1939 | France . |
| 1107833 | 3/1968 | United Kingdom . |

OTHER PUBLICATIONS

Photos of another bandage.

Primary Examiner—Robert A. Hafer
Assistant Examiner—Kerry Owens
Attorney, Agent, or Firm—Sprung Horn Kramer & Woods

[57] ABSTRACT

A clavicle bandage with two adjustable-length strips, wherein one end of each strip is secured to a ring that accordingly fastens the two together, in that the strips are made of a material that essentially does not stretch, and in that their free ends have means of establishing loops.

8 Claims, 2 Drawing Sheets

CLAVICLE BANDAGE

This is a continuation of U.S. application Ser. No. 461,722, filed Jan. 8, 1990, now abandoned.

The invention relates to a bandage for treating damage to the clavicle, primarily fractures, most of which occur in the form of oblique or splintered fractures in the middle third of the bone, where it is most curved. The major purpose is to stretch the clavicle longitudinally and immobilize it such that the surfaces of the break will fit and grow together rather than rubbing against each other.

What are called figure-eight bandages are often employed for bandaging injuries of this type. These articles are usually made from a tricot hose partly padded with cotton or from special hose bandages by the treating personnel themselves. Although such bandages are very cost-effective, they entail the drawback that the fabric stretches when subjected to tension, allowing the parts of the bone to displace again, so that the bandages, which take time to make, must be replaced several times before the bone can heal and must be tied twice at the rear, which is uncomfortable for a patient sleeping on his back.

There also exist a number of ready-made bandages, not all of which, however, completely satisfy the demands made on such an article. They are to some extent very expensive and bulky, have complicated fasteners and metal clasps that can lead to allergies, and are difficult or impossible to readjust.

The object of the present invention accordingly is to provide a clavicle bandage that is therapeutically reliable, meaning that it is anatomically secure and cannot shift or slide around, is easy to apply, is comfortable for the patient, and can easily be readjusted if necessary during the healing process.

This object is attained in accordance with the invention by a clavicle bandage with two adjustable-length strips, characterized in that one end of each strip is secured to a ring that accordingly fastens the two together, in that the strips are made of a material that essentially does not stretch, and in that their free ends have means of establishing loops.

The means of establishing loops in one especially preferred embodiment of the invention are Velcro-type barbed-tape fasteners.

One half of the fastener consists of a section of barbed tape mounted on the outside of the free end of each strip facing away from the patient's body and the other half consists of a section of tape that will adhere to the first section and extends along part of the rest of the strip.

It turns out to be practical for the section that adheres to the first section to extend over at least 1/6 of the strip.

The bandage will be especially easy to position if the total outer surface of the strips is made of a material to which the barbs on the other half of the fastener will adhere.

The ring at the center of the bandage to which the strips are secured, by means of a small loop with its end sewn tight for example, and through which the free ends of the strips are passed when the bandage is positioned, is preferably a flat, round, plastic ring. It can, however, also be a polygon, a hexagon or octagon for example.

There is a padded section approximately in the middle of the inside of the strip that faces the body. Since this section will be in the vicinity of the armpits when the bandage is in position, the padding should be made of an absorbent material, preferably cotton.

The bandage as a whole otherwise consists in a preferred embodiment of a layer of foam sandwiched between two layers of a looped or napped polyamide, goffered Nylon for example, and quilted. This material will not stretch, is comfortable against the skin, and is easy to wash.

A scale can be applied to the inside of the bandage as an aid to the physician, making it possible to establish, verify, and reproduce the length of and hence the tension on the bandage if it has to be removed.

The bandage in accordance with the invention will now be described by way of example with reference to the drawings, wherein.

Figure 1:
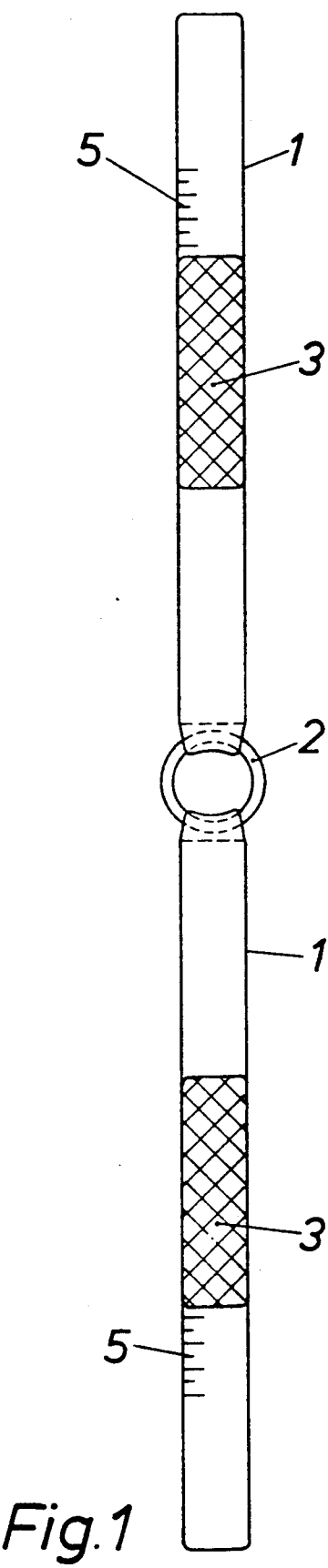
FIG. 1 is a schematic view of the side of the new bandage which faces the body.

Referring now more particularly to the drawings, as shown in FIG. 1, the bandage comprises two strips 1, a connecting ring 2, the pads 3, and a scale 5.

Figure 2:
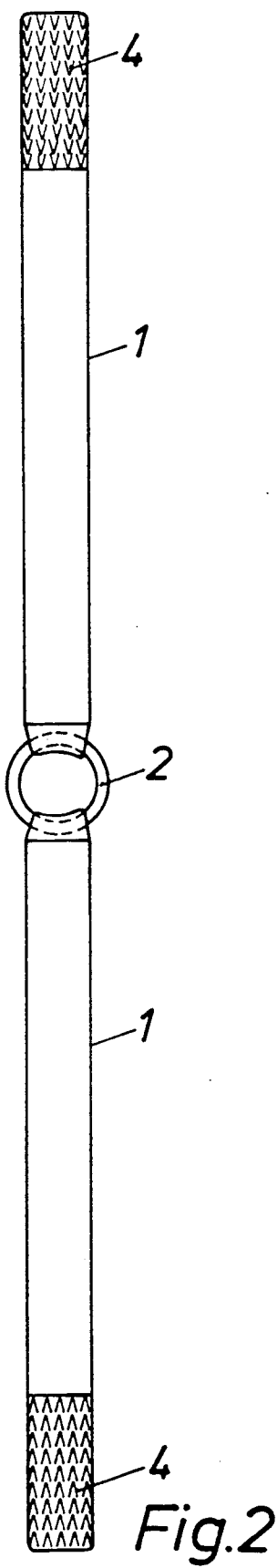
FIG. 2 is a schematic view of the side of the bandage of FIG. 1 which faces away from the body.

FIG. 2 illustrates the same bandage from the side that faces away from the body, illustrating strips 1, ring 2, and barbed tapes 4. The material that adheres to the barbs extends over the total outer surface of the strips.

The bandage ranges in overall length in its various sizes from approximately 1 to 1.80 m, the barbed strips being approximately 10 to 15 cm and the pads being approximately 20 to 40 cm long, the strips being approximately 5 cm wide and approximately 1 cm thick. The outside diameter of the ring is approximately 8 cm and its inside diameter approximately 7 cm.

Figure 3:
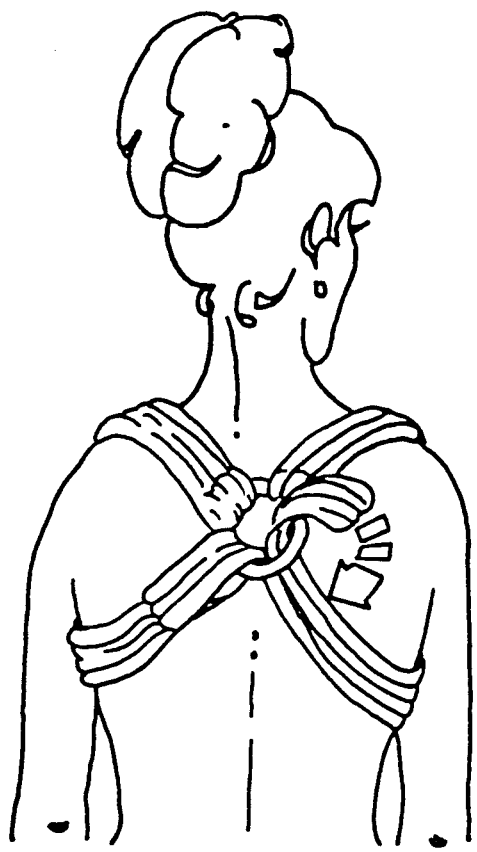
FIG. 3 is a view of the bandage applied to the body of a patient.

FIG. 3 illustrates how the bandage is positioned, the procedure being almost complete. The bandage is positioned around the patient's neck with the ring against her back. The free ends of the strips are passed under the arms from front to back and out through the ring with the strip on the intact side first and folded back with the two halves of the barbed fasteners together, creating loops. The two fasteners are then usually briefly disengaged again to establish uniform tension and finally engaged again once the optimal tension has been established and the bandage is correctly positioned.

The particular advantages of the clavicle bandage in accordance with the invention are its high therapeutic reliability, resulting from the tension-resistant and non-stretch fabric, which makes readjustments almost unnecessary and provides stability and perfect fit, and the simplicity provided by the barbed-tape fasteners. What is especially practical is that a long section of the outside of the strips is adhering, allowing one size bandage to be employed with many different patients. Another advantage is the flat ring, which does not provide bulk, does not annoy the recumbent patient, and, which is especially important, ensures that the strips will rest against the outer third of the clavicle and not against the fracture, which is generally at the midpoint of the bone. This repositions the fracture more effectively than with conventional bandages.

It will be understood that the specification and examples are illustrative but not limitative of the present invention and that other embodiments within the spirit and scope of the invention will suggest themselves to those skilled in the art.

What is claimed is:

1. A clavicle bandage consisting essentially of a ring, and two adjustable-length strips each secured at one end to the rings, the strips being essentially unstretchable and being provided at their ends with means for forming loops, said ring being flat so as to provide a means or positioning the strips against the outer third of the clavicle.

2. A bandage according to claim 1, wherein the means for forming loops are barbed-tape fasteners.

3. A bandage according to claim 2, wherein each barbed-tape fastener comprises first and second interacting sections, the first section being mounted on the outside of the free end of each strip facing away from the patient's body and the second section which will adhere to the first section extending along part of the rest of the strip.

4. A bandage according to claim 3, wherein the second section which adheres to the first section extends over at least 1/6 the length of the strip.

5. A bandage according to claim 3, wherein each strip has an inner and an outer surface and the total outer surface of each strip is formed of a material to which the barbs on the other half of the fastener will adhere.

6. A bandage according to claim 1, wherein the ring to which the strips are secured is a flat, round, plastic ring.

7. A bandage according to claim 1, including a padded section located approximately in the middle of the inside of the strip that faces the body and formed of an absorbent material.

8. A bandage according to claim 7, wherein the padded section is formed of cotton

* * * * *

UNITED STATES PATENT AND TRADEMARK OFFICE
CERTIFICATE OF CORRECTION

PATENT NO. : 5,133,340
DATED : July 28, 1992
INVENTOR(S) : KOOPMANN ET AL It is certified that error appears in the above-identified patent and that said Letters Patent is hereby corrected as shown below:

Col. 3 line 9    Delete " or " and substitute -- for --

Signed and Sealed this

Fifteenth Day of March, 1994

Attest:

BRUCE LEHMAN

Attesting Officer

Commissioner of Patents and Trademarks